(12) United States Patent
Jacob

(10) Patent No.: US 8,801,730 B2
(45) Date of Patent: Aug. 12, 2014

(54) RETENTION DEVICE, MEDICAL ROBOT AND METHOD TO SET THE TOOL CENTER POINT OF A MEDICAL ROBOT

(75) Inventor: Dirk Jacob, Marktoberdorf (DE)

(73) Assignee: Kuka Laboratories GmbH, Augsburg (DE)

( * ) Notice: Subject to any disclaimer, the term of this patent is extended or adjusted under 35 U.S.C. 154(b) by 800 days.

(21) Appl. No.: 12/604,462

(22) Filed: Oct. 23, 2009

(65) Prior Publication Data
US 2010/0106165 A1    Apr. 29, 2010

(30) Foreign Application Priority Data
Oct. 24, 2008   (DE) .......................... 10 2008 043 156

(51) Int. Cl.
   *A61B 19/00*    (2006.01)
   *A61G 15/00*    (2006.01)
   *A47C 20/00*    (2006.01)

(52) U.S. Cl.
   USPC ................................. 606/130; 128/845; 5/636

(58) Field of Classification Search
   USPC .............. 606/130, 1; 128/857, 845, 869, 897, 128/898; 5/87.1, 84.1, 636; 600/595
   See application file for complete search history.

(56) References Cited

U.S. PATENT DOCUMENTS

| | | | |
|---|---|---|---|
| 4,242,587 A * | 12/1980 | Lescrenier | 378/20 |
| 4,848,358 A * | 7/1989 | Nitzan et al. | 600/553 |
| 5,042,487 A * | 8/1991 | Marquardt | 600/425 |
| 5,194,792 A * | 3/1993 | Hara | 318/568.13 |
| 5,303,715 A * | 4/1994 | Nashner et al. | 600/595 |
| 5,997,176 A * | 12/1999 | Fairleigh | 378/196 |
| 6,029,670 A | 2/2000 | Anthony | |
| 6,454,718 B1 * | 9/2002 | Clift | 600/483 |
| 6,461,297 B1 * | 10/2002 | Pagnacco et al. | 600/300 |
| 6,796,947 B2 * | 9/2004 | Watt et al. | 600/552 |
| 6,800,062 B2 * | 10/2004 | Epley | 600/558 |
| 7,251,025 B2 * | 7/2007 | Jensen et al. | 356/241.1 |
| 7,559,766 B2 | 7/2009 | Epley et al. | |
| 8,265,321 B2 * | 9/2012 | Nystrom | 381/370 |
| 2002/0076059 A1 * | 6/2002 | Joynes | 381/71.6 |
| 2004/0138593 A1 * | 7/2004 | Maher | 601/1 |
| 2006/0251334 A1 | 11/2006 | Oba et al. | |
| 2007/0106184 A1 * | 5/2007 | Richard Vitton | 601/86 |
| 2007/0230660 A1 * | 10/2007 | Herrmann | 378/65 |
| 2008/0234865 A1 | 9/2008 | Sommer | |
| 2009/0272385 A1 * | 11/2009 | River et al. | 128/845 |
| 2009/0292194 A1 * | 11/2009 | Libbus et al. | 600/391 |
| 2010/0041961 A9 * | 2/2010 | Epley | 600/301 |
| 2010/0261978 A1 * | 10/2010 | Lithgow | 600/301 |
| 2011/0028872 A1 * | 2/2011 | Kevin | 601/86 |

* cited by examiner

*Primary Examiner* — Darwin Erezo
*Assistant Examiner* — Richard Louis
(74) *Attorney, Agent, or Firm* — Schiff Hardin LLP

(57) ABSTRACT

In a retention device, a medical robot and a method to set the tool center point of a medical robot, the retention device has a fixing device to fix the head of a person held by the retention device. The fixing device provides an indication of the position of the openings of the auditory canals of the ears of the person relative to the retention device based on the relation between the fixing device and the head of the person and the relation between the fixing device and the retention device.

5 Claims, 3 Drawing Sheets

RETENTION DEVICE, MEDICAL ROBOT AND METHOD TO SET THE TOOL CENTER POINT OF A MEDICAL ROBOT

BACKGROUND OF THE INVENTION

1. Field of the Invention

The present invention concerns a retention device, a medical robot and a method to set the tool center point of a medical robot.

2. Description of the Prior Art

Robots are generally work machines that can be equipped with tools for automatic handling and/or processing of subjects and are programmable in multiple movement axes, for example with regard to orientation, position and workflow. Robots typically possess programmable controllers (control devices) that control the movement workflow of the robot during the operation.

Moreover, robots are increasingly used in medical technology, for example as carriers of patient positioning systems. For example, DE 10 2005 041 606 A1 discloses a patient positioning device to position a patient in an exposure position for a radiation therapy system. The patient positioning device comprises a patient retention module and a positioning arm moving the patient retention module; a therapy control center controls the movement of said positioning arm.

In the field of otorhinolaryngological (ENT) medicine, different illnesses affecting the sense of equilibrium exist. One example of such an illness is benign paroxysmal positional vertigo (BPPV), in which affected persons suffer from rotatory vertigo as soon as they change the position of their heads. This rotatory vertigo is triggered by a separation of otolith particles of the utricular spot, which then causes an irritation of the nerve cells in the semicircular canals of the affected ear, which in turn causes the vertigo.

The complaint can be treated with therapy through a specific positioning of the affected persons. The particles separate as a result of a targeted and geometric sequence of repositionings of the affected person and are swept into a region of the vestibule of the vestibular labyrinth where they no longer cause complaints.

Depending on the affected semicircular canals, the affected person is repositioned in part by means of complex sequences. In particular, the repositionings associated with the vertical and rear semicircular canals can be implemented only barely or not at all. Moreover, a relatively precise positioning of the affected person and the time workflow of the repositioning are likewise relatively critical. In order to achieve a relatively good therapeutic success, the movement of the affected person should ensue relative to the center of the affected vestibular organ (equilibrium organ).

SUMMARY OF THE INVENTION

It is an object to provide a device that allows for an improved result in the treatment of the aforementioned positional vertigo.

The object of the invention is achieved in accordance with the invention by a retention device having a patient support that supports a person, and having a fixing device that fixes the head of a person held by the retention device relative to the patient support, the fixing device being configured to provide an indication of the position of the openings of the auditory canals of the ears of the person relative to the retention device, due to the known setting (relation) of the fixing device with the head of the person.

The invention also encompasses a medical robot having a retention device as described above, a control device, and a robot arm that has multiple axes and an attachment device controlled by the control device, the retention device being attached to the attachment device so as to also be controlled by the control device.

The invention also encompasses a method to set the tool center point of a robot that has a robot arm with an attachment device at which a retention device with a fixing device as described above is attached. In the method, the head of a person held with the retention device is fixed by means of the fixing device, the position of one of the two eardrums of the person is determined by means of measurement devices of the fixing device, relative to the retention device, the position of the hearing organ associated with the eardrum relative to the retention device is determined, and the tool center point of the robot is placed in the position of the hearing organ.

The retention device according to the invention, which is (for example) fashioned as a patient bed, carries the fixing device with which the head of the person can be fixed relative to the retention device. The retention device is fashioned such that a conclusion as to the positions of the openings of the auditory canals relative to the retention device is enabled based on its setting associated with the person. For example, this can be achieved by the fixing device having suitable automatic measurement devices that encompass the ears of the person as soon as his head is fixed with the fixing device. Such automatic measurement devices can be, for example, position measurement devices. It is also possible for an operator to read the position of the openings of the ears mechanically at the fixing device based on the mechanical setting of the fixing device, for example.

When the position of the opening of the ear whose hearing organ triggers the vertigo is known relative to the retention device, the position of the relevant hearing organ can then be determined based on this information in order, for example, to control the robot according to the invention so as to execute a movement relative to the position of the relevant hearing organ, this movement being designed for administering therapy to the person.

Based on the position (determined by means of the fixing device) of one of the openings of the auditory canals of the person, the robot according to the invention can then be set up to set the tool center point (whose movement in space can be controlled by means of the control device) in relation to this opening, in particular in the position of the relevant equilibrium organ.

The fixing device can have a measurement device that abuts the openings of the auditory canals in the setting associated with the head of the person and determines the distance to the eardrums of the person. Auditory canals of different persons are of different lengths. Requirements for an improved determination of the position of the eardrum associated with the hearing organ to be treated are satisfied due to this embodiment of the fixing device, so the position of the relevant hearing organ can likewise be determined more precisely relative to the retention device, and thus also relative to the robot. The measurement device is preferably based on a non-contact measurement method, for example laser or ultrasound, but contact-based measurement devices can also be used.

Based on the position (determined by means of the fixing device and the measurement device) of one of the eardrums of the person, the robot according to the invention can then be set up to set the tool center point (whose movement in space can be controlled by means of the control device) in relation to this eardrum, in particular in the position of the relevant equilibrium organ.

If the retention device according to the invention is a patient bed, the fixing device can have first displacement devices that allow a displacement of the measurement device in the direction of the longitudinal axis of the patient bed. The setting of the first displacement devices thus allows a conclusion to be made as to the position of the openings of the ears relative to the longitudinal axis of the patient bed.

In an embodiment of the retention device according to the invention, wherein measurement devices are used that emit signals that are a measure of the displacement of the measurement devices relative to the longitudinal axis are integrated into the first displacement devices, it is possible in a relatively simple and automated manner to determine the position of the openings of the ears relative to the longitudinal axis of the patient bed.

The fixing device can also have second displacement devices that allow a displacement of the measurement device in the direction of the transverse axis of the patient bed. The setting of the second displacement devices thus allows a conclusion to be made as to the position of the openings of the ears relative to the transverse axis of the patient bed.

In an embodiment of the retention device according to the invention, wherein measurement devices are used that emit signals that are a measure of the displacement of the measurement devices relative to the transverse axis are integrated into the second displacement devices, it is possible in a relatively simple and automated manner to determine the position of the openings of the ears relative to the transversal axis of the patient bed.

The fixing device can have third displacement devices that allow a displacement of the measurement device at a right angle to a surface of the patient bed on which the patient lies. The setting of the third displacement devices thus allows a conclusion to be made as to the position of the openings of the ears relative to the surface of the patient bed.

In an embodiment of the retention device according to the invention, wherein measurement devices are used that emit signals that are a measure of the displacement of the measurement devices relative to the surface of the patient bed are integrated into the third displacement devices, it is possible in a relatively simple and automated manner to determine the position of the openings of the ears relative to the transversal axis of the patient bed.

The fixing device can also be designed to have articulated arms, that embody (for example) measurement scales and/or angle transmitters to determine set angles, and that fix the head of the person. The measurement scales, or possibly measurement transmitters that are connected with the control device, provide the indication of the position of the openings of the auditory canals of the ears of the person.

DESCRIPTION OF THE PREFERRED EMBODIMENTS

Figure 1:
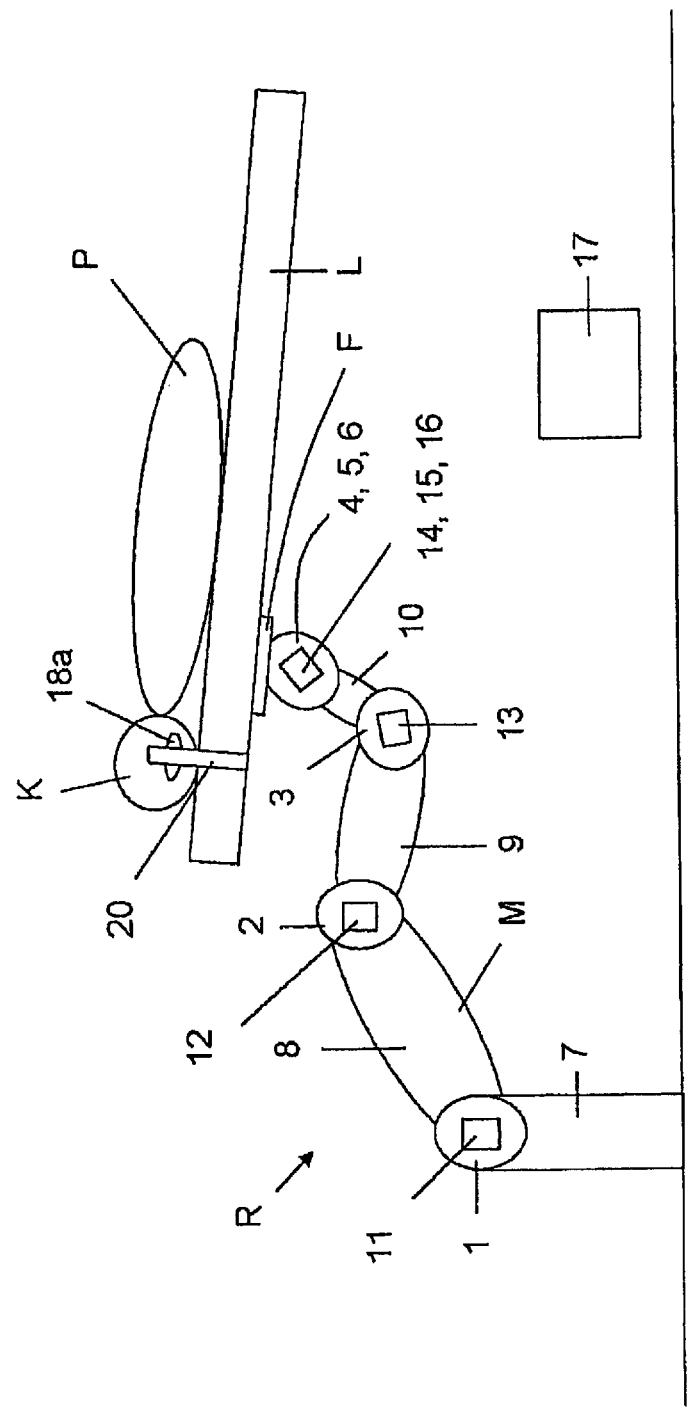
FIG. 1 shows a robot with a patient bed having a fixing device in accordance with the invention.
Figure 2:
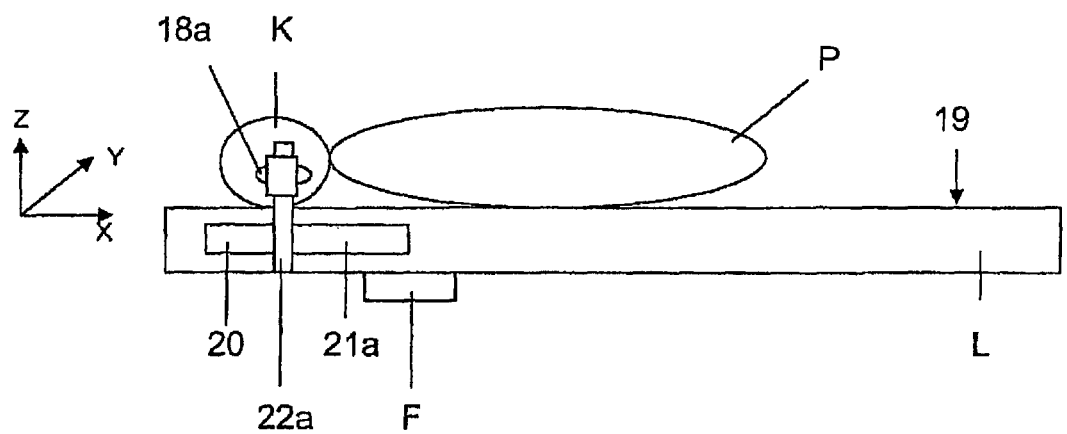
FIG. 2 is a side view of the patient bed of FIG. 1.
Figure 3:
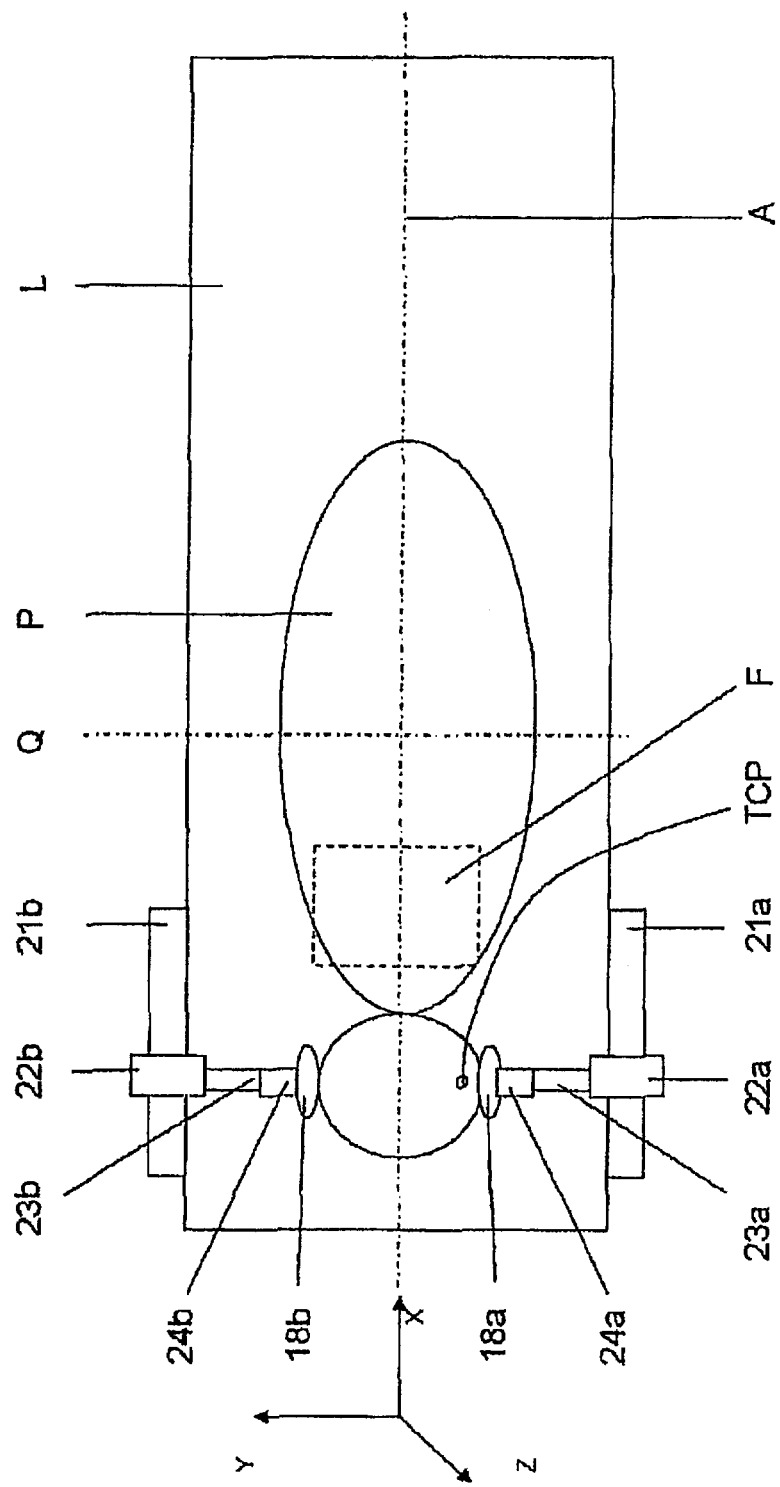
FIG. 3 is a plan view of the patient bed of FIGS. 1 and 2.

FIG. 1 shows a medical robot R with a robot arm M. The robot arm M essentially represents the movable part of the robot R and has multiple axes 1-6, multiple levers 7-10 and a flange F at which (in the case of the present exemplary embodiment) a patient bed L (shown in detail in FIGS. 2 and 3) is attached as an example of a patient retention device. FIG. 2 shows a side view and FIG. 3 shows a plan view of the patient bed L.

Each of the axes 1-6 is moved with an actuator (for example an electrical actuator) 11-16 that are connected (not shown) with a control computer 17 of the robot R so that the control computer 17 or a computer program running on the control computer 17 can control the electrical actuators 11-16 such that the position of the flange F of the robot R, and thus the patient bed L or, respectively, its tool center point TCP, can essentially be freely aligned in space. Each electrical actuator 11-16 of the robot R is formed, for example, by a motor and possibly power electronics activating the motor.

The patient bed L also has a fixing device 20, and a person P whose head K is fixed with the fixing device 20 so that the head K is essentially immobile relative to the patient bed L lies on the patient bed L.

Figure 4:
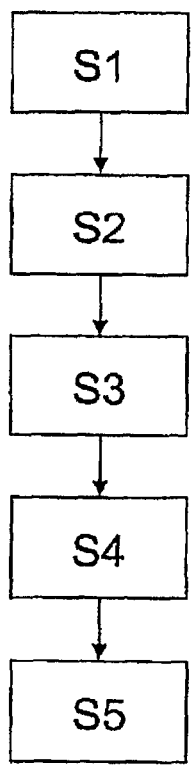
FIG. 4 is a flowchart illustrating the setting of the tool center point of the robot in accordance with the invention.

In the present exemplary embodiment, the control computer 17 is set up to adjust the tool center point TCP to the person P. The setting of the tool center point TCP adapted to the person P is summarized with a flowchart shown in FIG. 4.

In the present exemplary embodiment, the fixing device 20 has displacement devices in the form of longitudinal rails 21a, 21b aligned in the direction of the longitudinal axis A (x-direction) of the patient bed L. The longitudinal rails 21a, 21b are respectively attached to the sides of the patient bed L.

In the present exemplary embodiment, the fixing device 20 has displacement devices 22a, 22b that are supported such that they can be displaced in the longitudinal rails 21a, 21b so that the displacement devices 22a, 22b can be slid in the direction of the longitudinal axis A of the patient bed L.

In the case of the present exemplary embodiment, the displacement devices 23a, 23b are executed in a telescoping manner relative to the transversal axis Q (y-direction) aligned at a right angle to the longitudinal axis A, so as to interact with the displacement devices 22a, 22b. Measurement devices 24a, 24b respectively connected (not shown) with the control computer 17 are attached to the ends of said displacement devices 23a, 23b facing away from the sides of the patient bed L. The displacement devices 23a, 23b executed in a telescoping manner are coupled with the displacement devices 22a, 22b so that they can be displaced at a right angle to the longitudinal axis A and at a right angle to the transversal axis Q of the patient bed L. It is thus possible to align the measurement devices 24a, 24b at a desired distance from the surface 19 of the patient bed L (z-direction). The measurement devices 24a, 24b can be displaced in the direction of the transversal axis Q by means of the displacement devices 23a, 23b executed in a telescoping manner.

The fixing device 20 is provided to fix the head K of the person P relative to the patient bed L in that the measurement device 24a approaches the ear 18a and the measurement device 24b approaches the ear 18b of the person P.

If the head K of the person P is fixed, the position of the displacement devices 22a, 22b relative to the longitudinal axis A can be read, for example by means of a measurement scale (not shown) arranged at the longitudinal rails 21a, 21b. The longitudinal rails 21a, 21b can also or alternatively possess measurement sensors (not shown for the sake of clarity) connected with the control computer 17, as is provided in the present exemplary embodiment, the signals of which measurement sensors transmit to the control computer 17 information about the position of the displacement devices 22a, 22b relative to the longitudinal axis A of the patient bed L, and thus of the measurement devices 24a, 24b relative to the longitudinal axis A of the patient bed L.

The displacement devices 22a, 22b can likewise be a measurement scale based on which the position of the telescoping displacement devices 23a, 23b relative to the surface 19 of the patient bed L can be read. As is provided in the present embodiment, the displacement devices 22a, 22b can also or alternatively have measurement sensors (not shown for clarity) connected with the control computer 17 whose signals transmit to the control computer 17 information about the position of the telescoping displacement devices 23a, 23b relative to the surface 19 of the patient bed L, and thus of the measurement devices 24a, 24b relative to the surface 19 of the patient bed L.

The telescoping displacement devices 23a, 23b can likewise be a measurement scale based on which the position of the measurement devices relative to the transverse axis Q of the patient bed L can be read. As is provided in the present exemplary embodiment, the displacement devices 23a, 23b can also or alternatively possess measurement sensors (not shown for the sake of clarity) connected with the control computer 17 whose signals transmit to the control computer 17 information about the position of the measurement devices 24a, 24b relative to the transversal axis Q of the patient bed L. This enables the control computer 17 to determine the position of the measurement devices 24a, 24b relative to the patient bed L (Step S1 of the flowchart shown in FIG. 4).

Furthermore, the patient bed P is attached at the flange F of the robot R in a position known to the control computer 17 and is aligned in an orientation known to the control computer 17 so that the control computer 17 can determine the position of the measurement devices 24a, 24b relative to the flange F from the signals originating from the measurement sensors (Step S2 of the flowchart).

In the present exemplary embodiment, the measurement devices 24a, 24b lie at the ears 18a, 18b, and in particular at the openings of the ear canals (external auditory canals). In the case of the present exemplary embodiment, the measurement devices 24a, 24b are executed such that they in particular determine the length of the external auditory canals—thus the distance from the openings of the external auditory canals to the respective eardrums—without contact (Step S3 of the flowchart). Contact-free measurement methods are based on lasers or ultrasound, for example. Based on the signals originating from the measurement devices 24a, 24b, it is afterward possible for the control computer 17 to determine the positions of the eardrums of the ears 18a, 18b relative to the flange F of the robot R (Step S4 of the flowchart).

In the present exemplary embodiment, the control computer 17 is set up (configured) to place the tool center point TCP of the robot R at the position of one of the equilibrium organs (vestibular organs) of the ears 18a, 18b (Step S5 of the flowchart). Based on the position of the relevant eardrum, it is enabled for the control computer 17 to accordingly conclude the position of the relevant equilibrium organ relative to the patient bed L, and thus relative to the flange F, in order to set the tool center point TCP of the robot R at the position of the relevant equilibrium organ.

In the present exemplary embodiment, the control computer 17 is configured to activate the actuator 11-16 such that the tool center point TCP (and thus the person P lying on the patient bed L) conducts a predetermined movement.

Instead of the displacement devices in the form of longitudinal rails 21a, 21b and the displacement devices 23a, 23b, the fixing device 20 can be executed with a different design. An alternative embodiment of the fixing device 20 can also be such that this possesses articulated arms that, for example, comprise measurement scales and/or angle transmitters for the determination of set angles, and that this fixes the head K of the person P. The measurement scales or, respectively, in particular the measurement sensors connected with the control computer 17 allow a conclusion to be made as to the position of the openings of the auditory canals of the ears (18a, 18b) so that the robot R can suitably activate the axes 1-6 as necessary.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical robot comprising:
a retention device comprising
   a patient support configured to support a human patient thereon,
   a fixing device configured to fix the head of the patient on said patient support, said fixing device including a measurement device configured to abut the respective openings of the auditory canals of the ears of the patient to determine the position of the respective openings of auditory canals of the ears of the patient relative to the patient support, based on a determination of the position of the fixing device relative to the head of the patient and a determination of the position of the fixing device relative to the patient support,
   said retention device being configured to generate an electrical signal representing the position of the respective openings of auditory canals of the ears of the patient;
a control device supplied with said electrical signal representing said position;
a robot arm comprising multiple movement axes;
an attachment device that attaches said patient support to said robot arm; and
said control device being configured to operate said robot arm dependent on said indication position of the respective openings of auditory canals of the ears of the patient.

2. A medical robot as claimed in claim 1, wherein said control device is configured to set a tool center point of said robot arm, representing a point that is movable in space by controlling said robot arm with said control device, in relation to said openings of auditory canals of the patient.

3. A medical robot as claimed in claim 1, wherein said control device is configured to set said tool center point to coincide with a position of a predetermined equilibrium organ of the patient.

4. A medical robot as claimed in claim 1, wherein said measurement device is configured to determine the position of the respective ear drums of the patient by measuring the distance from the respective openings of the external auditory canals of the patient's ears to the respective eardrums of the patient, said measuring being a non-contact-based measurement, and wherein said control device is configured to set a tool center point of said robot arm, said tool center point being moved in space as said robot arm is operated by said control device, relative to the respective eardrums of the patient.

5. A medical robot as claimed in claim 4, wherein said control device is configured to set said tool center point to coincide with a position of a predetermined equilibrium organ of the patient.

* * * * *